United States Patent
Bornemann

(10) Patent No.: US 11,497,398 B2
(45) Date of Patent: Nov. 15, 2022

(54) METHOD AND DEVICE FOR CALIBRATING OPTICAL DIAGNOSTIC SYSTEM

(71) Applicant: ALCON INC., Fribourg (CH)

(72) Inventor: Stefan Bornemann, Erlangen (DE)

(73) Assignee: Alcon Inc., Fribourg (CH)

( * ) Notice: Subject to any disclaimer, the term of this patent is extended or adjusted under 35 U.S.C. 154(b) by 156 days.

(21) Appl. No.: 17/122,524

(22) Filed: Dec. 15, 2020

(65) Prior Publication Data
US 2021/0177258 A1 Jun. 17, 2021

Related U.S. Application Data

(60) Provisional application No. 62/948,727, filed on Dec. 16, 2019.

(51) Int. Cl.
*A61B 3/12* (2006.01)
*G06K 19/06* (2006.01)
*G06K 19/07* (2006.01)

(52) U.S. Cl.
CPC .......... *A61B 3/12* (2013.01); *G06K 19/06028* (2013.01); *G06K 19/06037* (2013.01); *G06K 19/0723* (2013.01)

(58) Field of Classification Search
CPC ............... A61B 3/12; G06K 19/06028; G06K 19/06037

USPC ......................................................... 702/104
See application file for complete search history.

(56) References Cited

U.S. PATENT DOCUMENTS

| 8,016,417 | B2 | 9/2011 | Reichert |
| 2011/0299038 | A1 | 12/2011 | Antkowiak et al. |
| 2016/0123894 | A1* | 5/2016 | Fu ..................... G01N 21/9501 356/615 |
| 2021/0263342 | A1* | 8/2021 | Ouderkirk ............. G02C 7/086 |

* cited by examiner

*Primary Examiner* — Allyson N Trail

(57) ABSTRACT

The present disclosure provides a device and method for calibrating an optical diagnostic system. The calibration device includes at least one pupil configured to receive light transmitted from an optical diagnostic system and to reflect the light back to the optical diagnostic system and a machine-readable label containing information to calibrate the optical diagnostic system, wherein the machine-readable label is disposed on the at least one pupil. The method includes positioning and aligning the optical diagnostic system with the calibration tool, scanning a machine-readable label disposed on at least one pupil of the calibration tool using the optical diagnostic system, storing setpoint values acquired from the machine-readable label into a storage medium of the optical diagnostic system, measuring actual values of the at least one pupil, comparing the actual values with the setpoint values, and determining that the actual values are within a tolerance of the setpoint values.

15 Claims, 5 Drawing Sheets

_US 11,497,398 B2_
1

METHOD AND DEVICE FOR CALIBRATING OPTICAL DIAGNOSTIC SYSTEM

TECHNICAL FIELD

The present invention generally relates to a calibration tool and, in particular, to a calibration tool for an optical diagnostic system.

BACKGROUND

Ophthalmologists work with optical diagnostic equipment on a daily basis to perform eye examinations for patients. In many cases, optical diagnostic equipment is periodically calibrated using a calibration tool (such as a test body, a test eye, a calibration target, or a reference body) to make sure that the optical diagnostic equipment provides accurate measurements. Therefore, the calibration tool is manufactured and measured with high precision. Due to the high accuracy required for the calibration tool, reproducibility of the calibration tool varies depending on production conditions. As a result of this variation, one calibration tool with predetermined setpoint/nominal values is typically assigned directly to a diagnostic system and another calibration tool cannot then be used with that system. This results in additional expenses and can make maintenance and repair of the optical diagnostic system more costly and complex and potentially less accurate, particularly if the assigned calibration tool is lost or if the incorrect tool is used.

SUMMARY

A calibration tool is disclosed. In one or more embodiments, the calibration tool includes at least one pupil configured to receive light transmitted from an optical diagnostic system and to reflect the light back to the optical diagnostic system. The calibration tool further includes a machine-readable label containing information to calibrate the optical diagnostic system, wherein the machine-readable label is disposed on the at least one pupil.

A method of calibrating an optical diagnostic system with a calibration tool is disclosed. The method includes positioning and aligning the optical diagnostic system with the calibration tool. The method further includes scanning a machine-readable label disposed on at least one pupil of the calibration tool using the optical diagnostic system. The method further includes storing setpoint values acquired from the machine-readable label into a storage medium of the optical diagnostic system. The method further includes measuring actual values of the at least one pupil. The method further includes comparing the actual values with the setpoint values. The method further includes determining that the actual values are within a tolerance of the setpoint values.

BRIEF DESCRIPTION OF THE DRAWINGS

Embodiments of the present disclosure are described by way of example in greater detail with reference to the attached figures, which are not necessarily to scale, and in which.

DETAILED DESCRIPTION OF THE INVENTION

The present disclosure is directed to a calibration tool for an optical diagnostic system. More particularly, embodiments of the present disclosure are directed to a calibration tool configured to calibrate multiple optical diagnostic systems in a semi-automatic manner.

The calibration of the optical diagnostic system is performed with the calibration tool equipped with a pupil, which mimics a pupil in an eye. The pupil of the calibration tool has fixed parameters (such as setpoint values, nominal values, an axial length of a pupil, a pupil diameter, a radius of curvature of a ball, or refractive error). Embodiments of the present disclosure allow one calibration tool to calibrate multiple optical diagnostic systems with a machine-readable label disposed on the pupil of the calibration tool. The machine-readable label includes information for the calibration (such as a serial number of a calibration tool, a product number of a calibration tool, and the fixed parameters of the pupil).

Additionally, embodiments of the present disclosure are directed to a method of calibrating an optical diagnostic system using a calibration tool. More particularly, embodiments of the present disclosure are directed to a method of calibrating an optical diagnostic system using a calibration tool by (a) positioning and aligning the optical diagnostic system with the calibration tool; (b) scanning a machine-readable label disposed on at least one pupil of the calibration tool using the optical diagnostic system; (c) storing setpoint values acquired from the machine-readable label in a storage medium of the optical diagnostic system; (d) measuring actual values of the pupil in the calibration tool; (e) comparing the actual values with the setpoint values; and (f) determining that the actual values are within a tolerance of the setpoint values.

Referring now to the description and drawings, example embodiments of the disclosed apparatuses, systems, and methods are shown in detail.

Figure 1A:
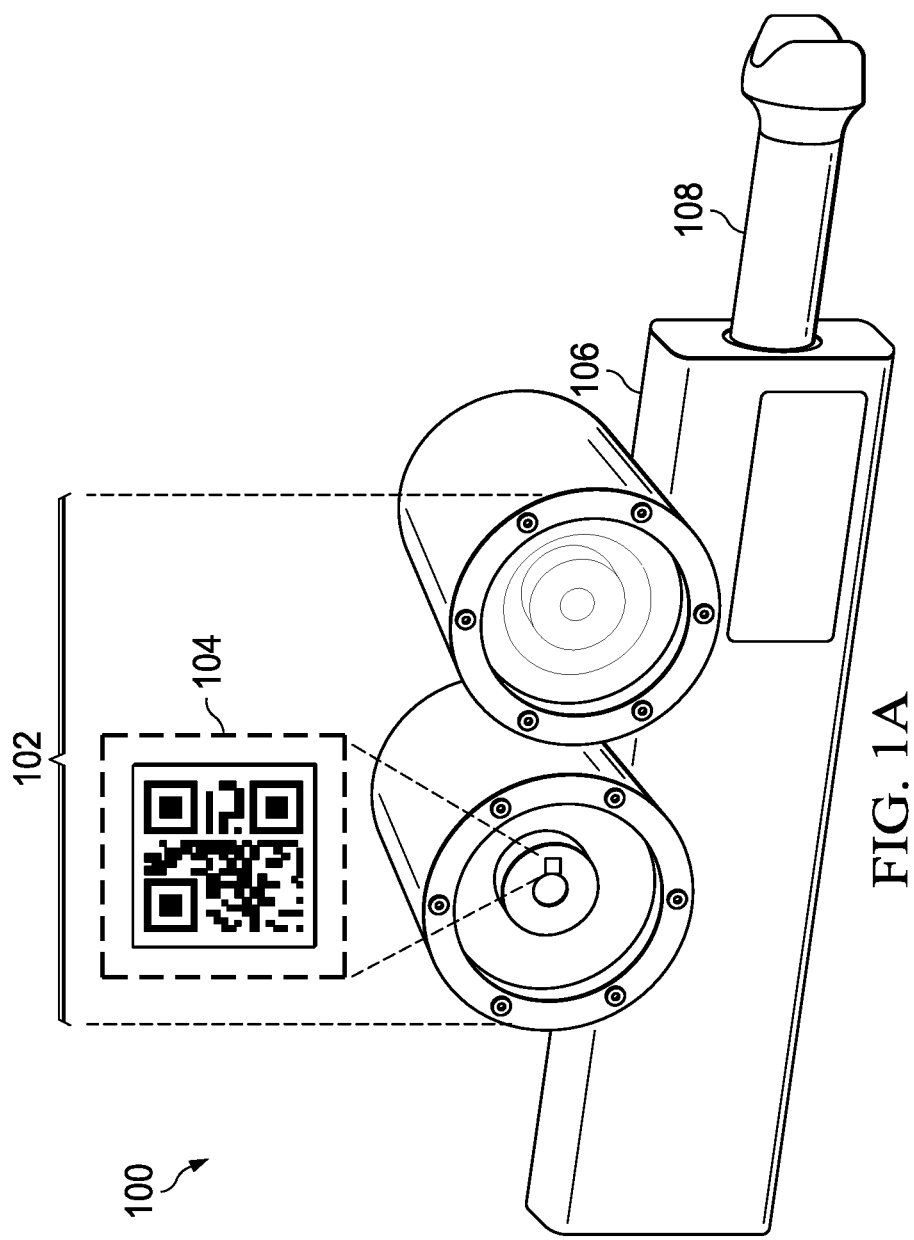
FIG. 1A is an illustration of a calibration tool, in accordance with one or more embodiments of this disclosure.

FIG. 1A illustrates a calibration tool 100, in accordance with one embodiment of the present disclosure. The calibration tool 100 may be suitable for calibrating multiple optical diagnostic systems. For example, the calibration tool 100 may be suitable for calibrating a first optical diagnostic system, which may be at a location A and a second optical diagnostic system, which may be at a location B. This avoids the need for a specific, individual calibration tool for each individual optical diagnostic system. In this regard, embodiments of the present disclosure allow for calibrating at least two optical diagnostic systems which are not physically in the same location.

In one embodiment, the calibration tool 100 includes pupils 102. For example, the pupils 102 of the calibration tool 100 may include at least one pupil 102 configured to receive light suitable for measurements of the eye of a patient using an optical diagnostic system. For instance, the light received on the pupils 102 may be illuminated from the optical diagnostic system. The pupils 102 may reflect the light back to the optical diagnostic system.

In some embodiments, the calibration tool 100 may include parts similar to a human eye to accurately calibrate the optical diagnostic. For example, the calibration tool 100 may have pupils 102 which include features that mimic the human eye, such as a rod lens, or a ball. In this example, the construction of the pupils 102 of the calibration tool 100 imitates human eyes so that the pupils 102 receive light from and reflect the light to the optical diagnostic system as the human eyes would.

It is noted that while the pupils 102 illustrated in FIG. 1A may include two pupils, such a configuration is merely provided for illustrative purposes. The embodiments of the present disclosure may be configured to include only one (FIG. 1B) or three or more pupils. Further, it is noted that while the pupils 102 illustrated in FIG. 1A are aligned horizontally, such a configuration is merely provided for illustrative purposes. The embodiments of the present disclosure may be configured to align the pupils 102 vertically or in any other orientation. The number and orientation of the pupils 102 may differ based on requirements of optical diagnostic systems or to facilitate manufacturing or durability of the calibration tool 100.

In one embodiment, the calibration tool 100 includes a machine-readable label 104. For example, the machine-readable label 104 such as a data matrix code may be a barcode containing information to conduct a calibration of an optical diagnostic system. For instance, the barcode of the machine-readable label 104 may be a data matrix barcode such as a two-dimensional barcode. In another instance, the barcode of the machine-readable label 104 may be a linear barcode such as a one-dimensional barcode.

The machine-readable label 104 of the calibration tool 100 may be disposed on the pupils 102 such that the machine-readable label 104 can be read by the optical diagnostic system. For example, the machine-readable label 104 may be disposed on a surface proximate to the pupils 102 as shown in FIG. 1A.

The machine-readable label 104 of the calibration tool 100 may include information for calibrating an optical diagnostic system. For example, the information contained in the machine-readable label 104 may include a serial number of a calibration tool, a product number of a calibration tool, setpoint values, nominal values, an axial length of a ball in the calibration tool, a pupil diameter of the calibration tool, a radius of curvature of the ball in the calibration tool, or refractive error of the ball in the calibration tool. The length of the rod lens is the reference standard for the axial length of the pupil and the radius of curvature of the ball is the reference standard for the radius of curvature of the cornea. When the machine-readable label 104 is scanned by a camera of the optical diagnostic system, the information for calibrating the optical diagnostic system may be stored in a storage medium of the optical diagnostic system. In this regard, the information included in the machine-readable label 104 is unique to one calibration tool 100. This specificity of the information may be due to the high accuracy exhibited by the calibration tool.

In some embodiments, the machine-readable label 104 of the calibration tool 100 may utilize radio frequency technologies to communicate with an optical diagnostic system. For example, radio frequency technologies used for the machine-readable label 104 of the calibration tool 100 may include radio frequency identification (RFID), or Near-field communication (NFC).

It is noted that while the machine-readable label 104 illustrated in FIG. 1A is disposed only on one of two pupils, such a configuration is merely provided for illustrative purposes. The embodiments of the present disclosure may be configured to have multiple machine-readable labels 104 for the calibration tool 100. For example, a first machine-readable label may be disposed on a first pupil, while a second machine-readable label may be disposed on a second pupil. As described above, each pupil is equipped with a unique machine-readable label. In a configuration where there is a total of two pupils with unique machine-readable labels, one of the two pupils may be used as a backup pupil. For instance, in case that a first calibration fails with the first pupil, the second pupil may be used to carry out a further calibration for the optical diagnostic system. By way or another example, the calibration tool equipped with two different machine-readable labels may allow for calibrating two optical diagnostic systems at the same time.

In one embodiment, the calibration tool 100 includes a body assembly 106 configured to stabilize pupils 102. For example, the pupils 102 may be supported by the body assembly 106, as shown in FIG. 1A. The pupils 102 may be fixed onto a surface of the body assembly 106. For example, the pupils may be fixed on top of a body assembly. The body assembly 106 may be at least partially in direct contact with the pupils 102. By way of another example, the body assembly 106 and the pupils 102 may be integrated together to stabilize the pupils. For instance, the pupils 102 may be integrated into the body assembly 106 so that the pupils 102 may be embedded within the body assembly 106.

In one embodiment, the calibration tool 100 includes a rod 108 to be secured to a chin rest bar holder 206 of an optical diagnostic system. The chin rest bar of the optical diagnostic system is a place for a patient to place his or her chin when an ophthalmologist examines the patient's eyes. The calibration for the optical diagnostic system is typically performed by first securing the calibration tool 100 onto the chin rest bar holder 206 of the optical diagnostic system. In this regard, the rod 108 of the calibration tool 100 securely anchors the calibration tool 100 to the optical diagnostic system. The rod 108 of the calibration tool 100 may be used together with the body assembly 106, as shown in FIG. 1A. For example, a middle part of the rod 108 may be covered by the body assembly 106. This may allow the body assembly 106 to slide horizontally to adjust its location relative to the optical diagnostic system so that the pupils 102 align with a camera of the optical diagnostic system.

Figure 1B:
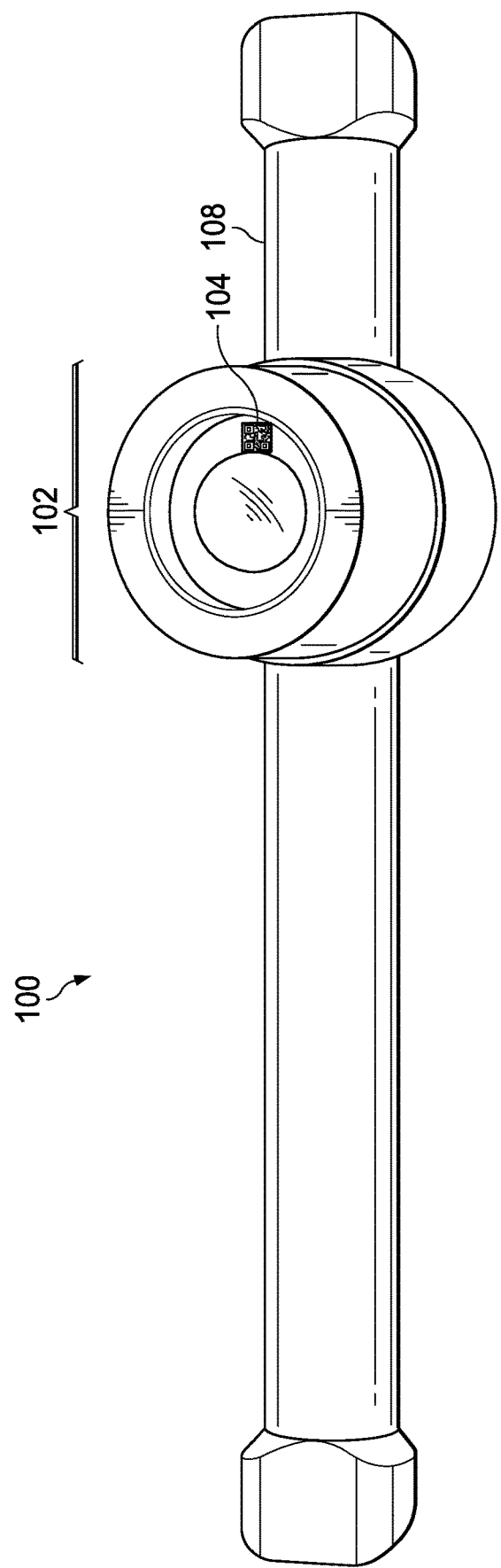
FIG. 1B is an illustration of another calibration tool, in accordance with one or more embodiments of this disclosure.

While both the rod 108 and the body assembly 106 illustrated in FIG. 1A are used for the calibration tool 100, such a configuration is merely provided for illustrative purposes. The embodiments of the present disclosure may be configured to use only the rod 108 to stabilize the pupil 102 as shown in FIG. 1B. FIG. 1B illustrates another calibration tool, in accordance with another embodiment of the present disclosure. As long as the pupil 102 is securely attached to a chin rest bar holder 206 of an optical diagnostic system for calibration, the body assembly 106 may be omitted. Instead, the rod 108 may support the pupil 102.

Figure 2:
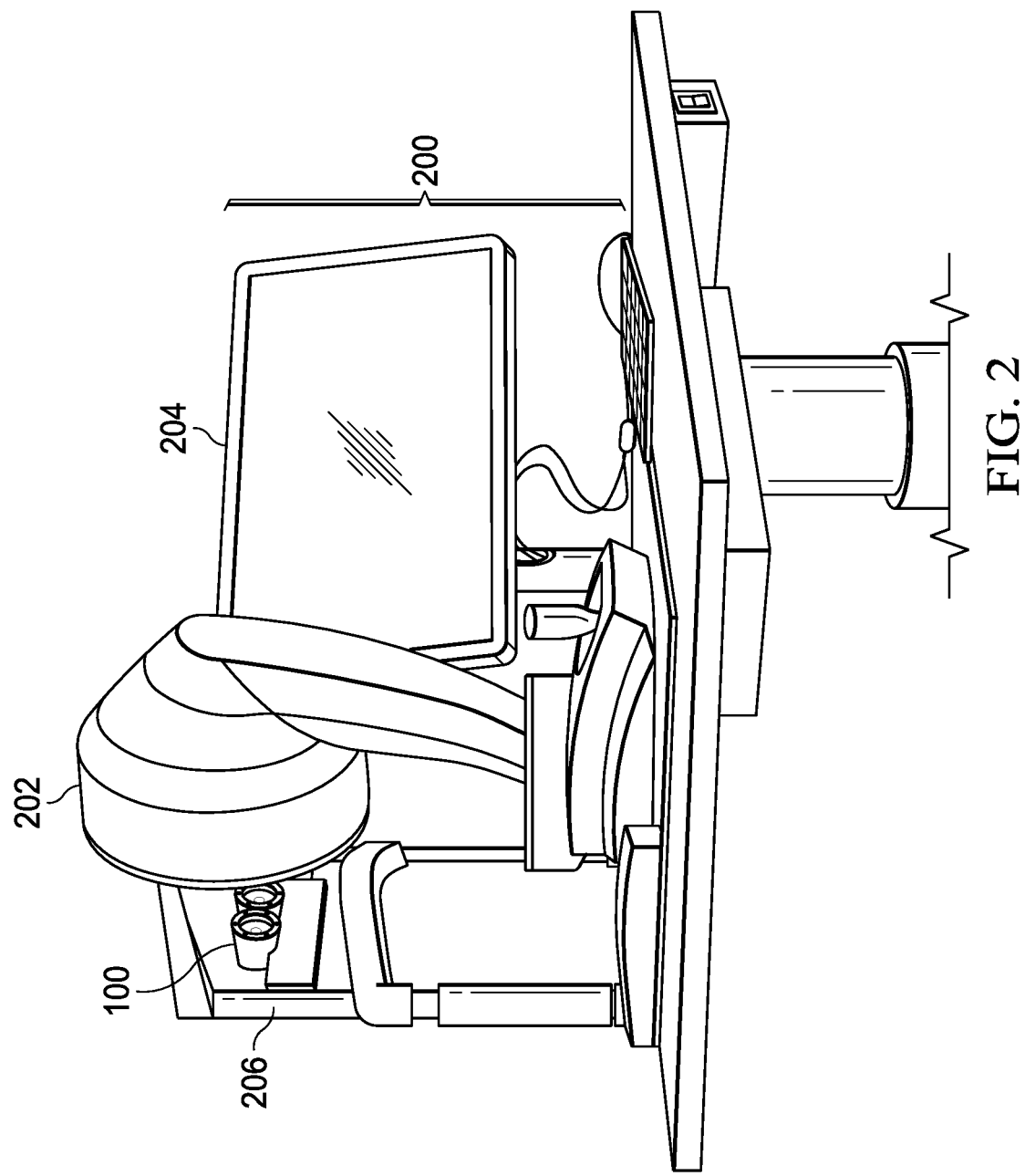
FIG. 2 is an illustration of a calibration setup of an optical diagnostic system with a calibration tool, in accordance with one or more embodiments of this disclosure.

FIG. 2 generally illustrates a calibration setup of an optical diagnostic system 200 with a calibration tool 100, in accordance with one or more embodiments of the present disclosure. The calibration tool 100 is arranged to calibrate the optical diagnostic system 200. For example, the calibration tool 100 may be securely attached to a chin rest bar holder 206 of the optical diagnostic system 200. Lens of the pupils may face toward a camera 202 of the optical diagnostic system 200, which allows a machine-readable label disposed on the pupils 102 of the calibration tool 100 to be scanned by the optical diagnostic system 200. The machine-readable label on the pupils 102 is a certain height above a reference point, such as the floor. The height of the camera 202 of the optical diagnostic system 200 is aligned with that of the machine-readable label. The location of the calibration tool 100 is also aligned with the optical diagnostic system 200 such that the optical diagnostic system 200 can scan at least one pupil 102. If the height of the machine-readable label of the calibration tool 100 and the height of the camera of the optical diagnostic system 200 are not properly aligned, the height, location, or both of the calibration tool 100 may be adjusted. For instance, the height of the calibration tool 100 may be adjusted by either lifting or lowering the calibration tool on the chin rest bar holder 206. In another instance, the location of the calibration tool 100 may be adjusted by sliding the body assembly of the calibration tool 100 or moving the chin rest bar holder 206 location.

In one embodiment, the optical diagnostic system 200 includes a monitor 204. The monitor 204 of the optical diagnostic system 200 may show a calibration procedure, a control measurement wizard for a calibration, captured images from the camera 202, or diagnostic-related windows. For example, when a user starts a calibration process, a control measurement wizard may appear on the monitor 204 and within the wizard there may be specific instructions on how to proceed with the calibration. By way of another example, when the machine-readable label of the calibration tool 100 is scanned by the camera 202 of the optical diagnostic system 200, the control measurement wizard may open automatically and display the information stored in the machine-readable label on the monitor 204. The monitor 204 of the optical diagnostic system 200 may also show windows not related to the calibration process such as web browsing, video streaming, gaming, and general computer use.

In some embodiments, the optical diagnostic system 200 includes a storage medium that includes calibration data. The optical diagnostic system 200 also includes a processor coupled to the storage medium. The processor is configured to compare data (such as actual values) acquired by the camera of the optical diagnostic system with data (such as setpoint/nominal values) included in the machine-readable label of the calibration tool. The processor is also configured to determine whether the calibration is successful based on the data acquired by the camera of the optical diagnostic, the data included in the machine-readable label, and tolerances previously established for the calibration.

Figure 3:
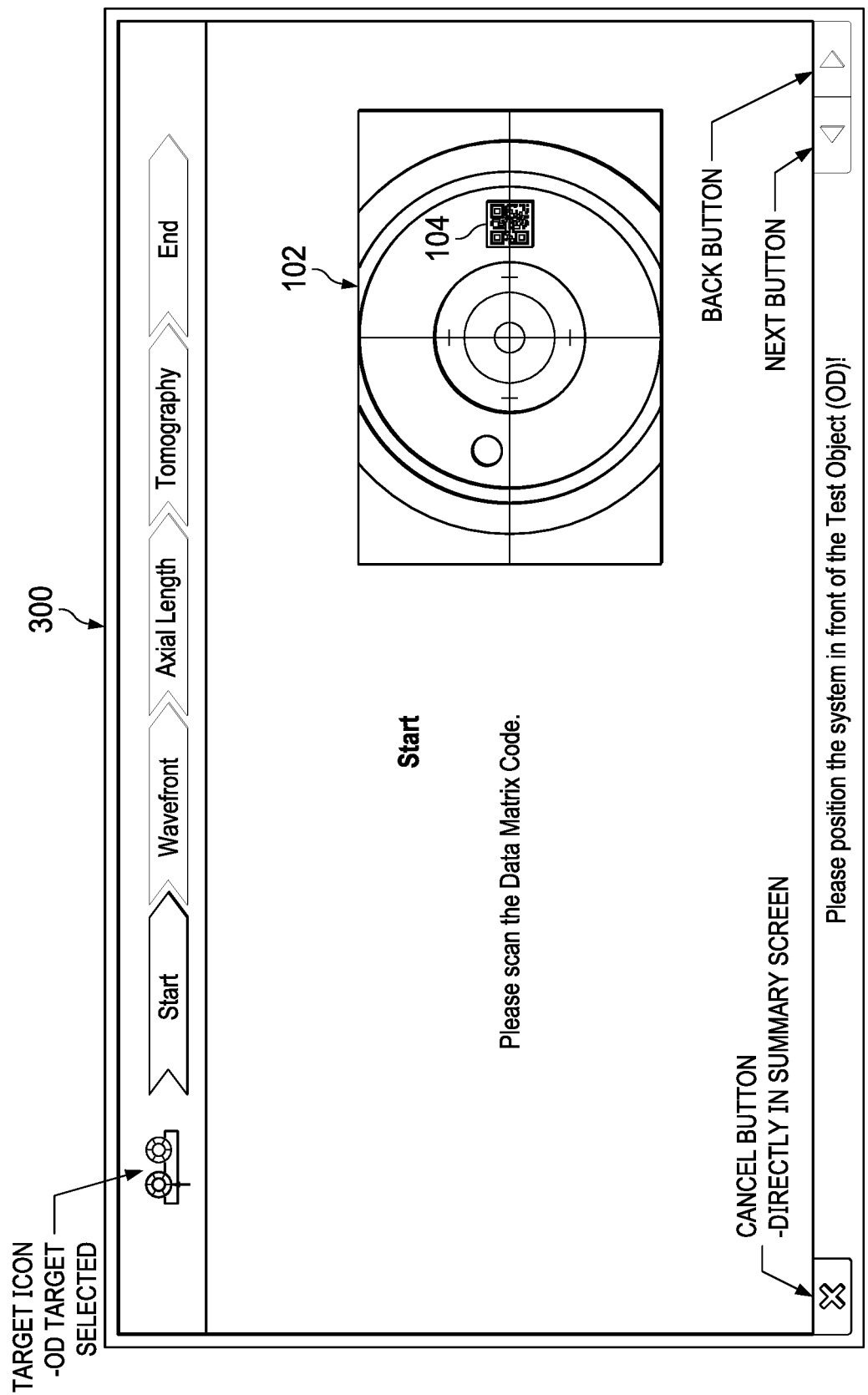
FIG. 3 is an illustration of a control measurement wizard used for a calibration of an optical diagnostic system, in accordance with one or more embodiments of this disclosure.

FIG. 3 generally illustrates a control measurement wizard 300 used for a calibration of an optical diagnostic system, in accordance with one or more embodiments of the present disclosure. The control measurement wizard 300 is a user interface implemented in the optical diagnostic system which leads the user through a series of well-defined calibration steps. For example, the control measurement wizard 300 may instruct a user to scan the machine-readable label 104 disposed on the pupil 102 to start a calibration process for the optical diagnostic system. Once the machine-readable label is scanned and the relevant information is stored in a storage medium of the optical diagnostic system, the optical diagnostic system measures actual values. The optical diagnostic system then compares the actual values measured by the optical diagnostic system with the setpoint values from the machine-readable label to determine if the calibration is successfully performed. In this regard, an implementation of the control measurement wizard 300 in the calibration steps makes the process easier to follow and would allow for a daily or weekly calibration. Once the user aligns the camera of the optical diagnostic system with the pupil and the machine-readable label of the calibration tool, the rest of the calibration steps may be semi-automatic in that the interaction needed from the user is minimum. In this sense, embodiments of the present disclosure may allow for an automatic calibration of an optical diagnostic system.

While the initial screen for calibration steps on the control measurement wizard 300 is shown in FIG. 3, such a configuration is merely provided for illustrative purposes. Embodiments of the present disclosure may be configured to provide a series of instructions to complete the calibration process.

Figure 4:
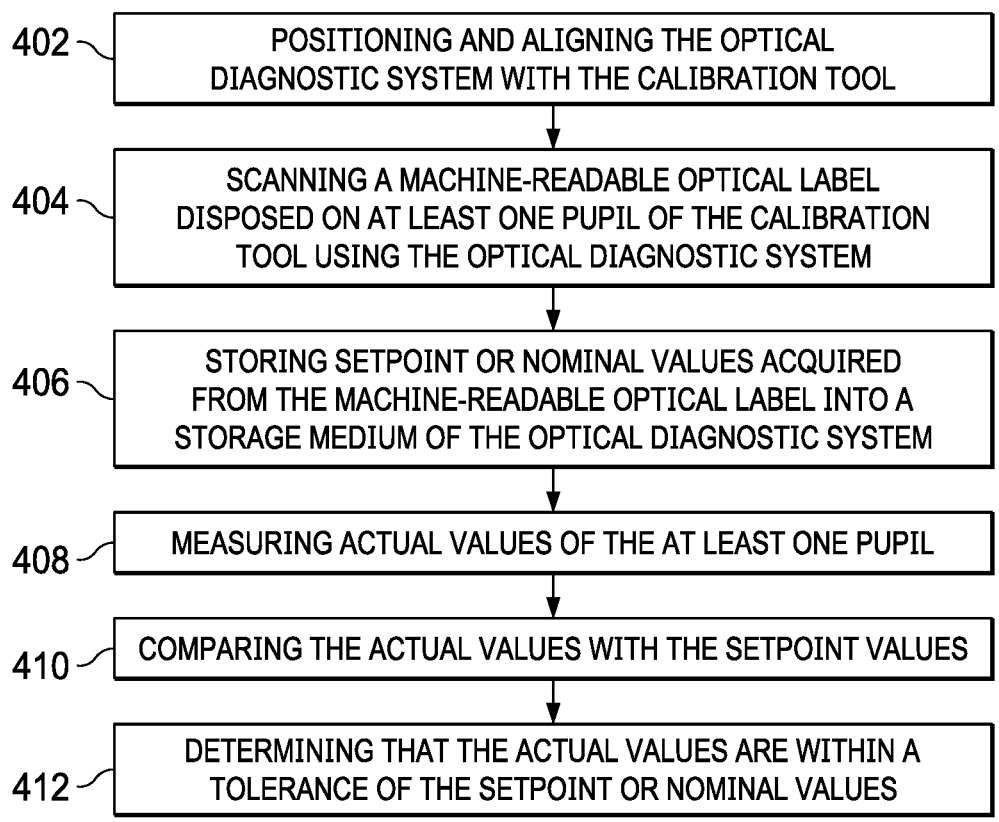
FIG. 4 is a flow chart illustrating a method of calibrating an optical diagnostic system with a calibration tool, in accordance with one or more embodiments of this disclosure.

FIG. 4 illustrates a method for calibrating an optical diagnostic system with a calibration tool, in accordance with one or more embodiments of the present disclosure. The optical diagnostic system or calibration tool or both used in this method may be as described in FIGS. 1-3. It is noted that all of the steps shown in FIG. 4 are not essential to practice the method. One or more steps may be omitted from or added to the method illustrated in FIG. 4, and the method can still be practiced within the scope of this embodiment. Further, some of the steps may be performed in a different order and the method can still be practiced within the scope of this embodiment. For example, the method may be configured to start by scanning a machine-readable label disposed on at least one pupil of the calibration tool using the optical diagnostic system 404 first. Then, the optical diagnostic system is positioned and aligned with the calibration tool 402.

The method shown in FIG. 4 generally includes positioning and aligning the optical diagnostic system with the calibration tool. The method also includes scanning a machine-readable label disposed on at least one pupil of the calibration tool using the optical diagnostic system. The method further includes storing setpoint values acquired from the machine-readable label into a storage medium of the optical diagnostic system. The method includes measuring actual values of the pupil in the calibration tool. The method additionally includes comparing the actual values with the setpoint values. Further, the method includes determining that the actual values are within a tolerance of the values.

As shown in step 402 of FIG. 4, the method includes positioning and aligning the optical diagnostic system with the calibration tool. Positioning and aligning the optical diagnostic system with the calibration tool may be performed by a user. The location of the calibration tool 100 is aligned with the optical diagnostic system 200 such that the optical diagnostic system 200 can scan at least one pupil 102. The pupil on the calibration tool may be cleaned and checked for visible damages prior to starting a calibration. Additionally, the calibration is best performed with no external reflections on the pupils of the calibration tool, such as in dimmed ambient light conditions.

As shown in step 404 of FIG. 4, the method includes scanning a machine-readable label disposed on at least one pupil on the calibration tool using the optical diagnostic system. Scanning a machine-readable label disposed on at least one pupil on the calibration tool may be performed by a camera within the optical diagnostic system. The machine-readable label of the calibration tool may include information for conducting a calibration for an optical diagnostic system. For example, the information contained in the machine-readable label may include an axial length of the at least one pupil, a diameter of the at least one pupil, a radius of curvature of a ball, and a refractive error. A control measurement wizard may be utilized to instruct a user to scan the machine-readable label disposed on the pupil to start a calibration process for the optical diagnostic system.

Further, as shown in step 406 of FIG. 4, the method includes storing setpoint values acquired from the machine-readable label into a storage medium of the optical diagnostic system. Setpoint values acquired from the machine-readable label may be written in an initial/log-file portion of the storage medium.

As shown in step 408 of FIG. 4, the method includes measuring actual values of the pupil in the calibration tool. The actual values may include measurements of, an axial length of a ball in the calibration tool, a radius of curvatures of a cornea on the ball, a refractive error of the ball, and a pupil diameter.

As shown in step 410 of FIG. 4, the method includes comparing the actual values with the setpoint values. The setpoint values scanned from the machine-readable label and stored in the initial/file-log portion of the storage may be compared with the actual values measured by the optical diagnostic system. For example, the measured axial length of the ball in the calibration tool may be compared to a length of a rod lens stored in the machine-readable label. By another example, the measured radius of curvature of the cornea on the ball may be compared to a radius of curvature of the ball stored in the machine-readable label. By yet another example, the measured refractive error may be compared to a refractive error of the calibration tool stored in the machine-readable label. By another example, the measured pupil diameter may be compared to a pupil diameter stored in the machine-readable label.

Additionally, as shown in step 412 of FIG. 4, the method includes determining that the actual values are within a tolerance of the setpoint values. The tolerance may be determined based on requirements set by the optical diagnostic system, set by the calibration tool, set by manufacturers or users, or set by regulations in optics field. If the actual values are within the tolerance of the setpoint values, the calibration process is complete and now the optical diagnostic system is properly calibrated. If the actual values are outside the tolerance of the values, the control measurement wizard may prompt the user to repeat steps 408-412 of the method to recalibrate the system.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although a user is described herein as a single figure, those skilled in the art will appreciate that the user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed:

1. A calibration tool comprising:
    at least one pupil configured to receive light transmitted from an optical diagnostic system and to reflect the light back to the optical diagnostic system; and
    a machine-readable label containing information to calibrate the optical diagnostic system, wherein the machine-readable label is disposed on the at least one pupil.

2. The calibration tool of claim 1, wherein the information on the machine-readable label includes at least one of a serial number, a product number, and setpoint values.

3. The calibration tool of claim 2, wherein the setpoint values include at least one of an axial length of the at least one pupil, a diameter of the at least one pupil, a radius of curvature of a ball, and a refractive error.

4. The calibration tool of claim 1, wherein the machine-readable label is at least one of a linear barcode, a data matrix barcode, or a radio-frequency identification.

5. The calibration tool of claim 1, wherein the information on the machine-readable label is scanned by a camera of the optical diagnostic system.

6. The calibration tool of claim 1, wherein the information on the machine-readable label is configured to be stored in a log file of the optical diagnostic system.

7. The calibration tool of claim 1, wherein the calibration tool is a portable device.

8. The calibration tool of claim 1, further comprising:
a body assembly configured to support the at least one pupil, wherein the body assembly is fixed to the at least one pupil.

9. A method of calibrating an optical diagnostic system with a calibration tool, comprising:
(a) positioning and aligning the optical diagnostic system with the calibration tool;
(b) scanning a machine-readable label disposed on at least one pupil of the calibration tool using the optical diagnostic system;
(c) storing setpoint values acquired from the machine-readable label into a storage medium of the optical diagnostic system;
(d) measuring actual values of the at least one pupil;
(e) comparing the actual values with the setpoint values; and
(f) determining that the actual values are within a tolerance of the setpoint values.

10. The method of claim 9, wherein the setpoint values on the machine-readable label include at least one of an axial length of the at least one pupil, a diameter of the at least one pupil, a radius of curvature of a ball, and a refractive error, wherein the actual values include at least one of an axial length of the at least one pupil, a diameter of the at least one pupil, a radius of curvature of a ball, and a refractive error.

11. The method of claim 9, wherein the machine-readable label is at least one of a linear barcode, a data matrix barcode, or a radio-frequency identification.

12. The method of claim 9, wherein the machine-readable label is scanned by a camera of the optical diagnostic system.

13. The method of claim 9, wherein the setpoint values on the machine-readable label are stored in a log file of the storage medium of the optical diagnostic system.

14. The method of claim 9, wherein the calibration tool is a portable device.

15. The method of claim 9, wherein the method is facilitated by a control measurement wizard.

\* \* \* \* \*